United States Patent [19]

Imade et al.

[11] Patent Number: 4,683,751

[45] Date of Patent: Aug. 4, 1987

[54] SAMPLE STAND ADJUSTING DEVICE IN AN ULTRASONIC MICROSCOPE

[75] Inventors: Shinichi Imade, Hachioji; Kouichi Karaki, Hino, both of Japan

[73] Assignee: Olympus Optical Co., Ltd., Tokyo, Japan

[21] Appl. No.: 861,802

[22] Filed: May 12, 1986

[30] Foreign Application Priority Data

May 14, 1985 [JP] Japan ................ 60-102041

[51] Int. Cl.$^4$ ............................ G01N 29/04
[52] U.S. Cl. ...................... 73/606; 73/607; 73/634; 73/629
[58] Field of Search ............. 73/606, 627, 629, 633, 73/634, 607

[56] References Cited

U.S. PATENT DOCUMENTS

| | | | |
|---|---|---|---|
| 4,378,699 | 4/1983 | Wickramasinghe | 73/606 |
| 4,459,852 | 7/1984 | Chubachi et al. | 73/606 |
| 4,491,020 | 1/1985 | Chubachi | 73/606 |

FOREIGN PATENT DOCUMENTS 59-225349  4/1983  Japan .

*Primary Examiner*—Howard A. Birmiel
*Attorney, Agent, or Firm*—Armstrong, Nikaido, Marmelstein & Kubovcik

[57] ABSTRACT

In an ultrasonic microscope, if a plane to be observed of a sample is not parallel with a scanned plane formed by an ultrasonic wave beam, an interference with a reflected wave will be produced and no clear picture image will be obtained. Therefore, it is indispensable to adjust the inclination of the sample stand as an initial adjustment before the observation. In the present invention, for this adjustment, an acoustic lens is focused at any one point o of a sample mounted on the sample stand, then a distance Zo between the acoustic lens and sample is measured and memorized and the relative displacement Xa of the sample and acoustic lens from the point o to a point a in the X-direction, the relative displacement Yb in the Y-direction and the relative moving distances Za-Zo ad Za-Zb (wherein Za and Zb are distances between the respective points a and b and the acoustic lens) of the above mentioned acoustic lens and the sample in the Z-direction when the acoustic lens is focused at the respective points a and b are measured and memorized. The inclination of the sample is known on the basis of the scalar data of these respective measured and memorized distances and the required adjusting amount is monitored and indicated so that the adjustment may be easily made without requiring a skill.

3 Claims, 12 Drawing Figures

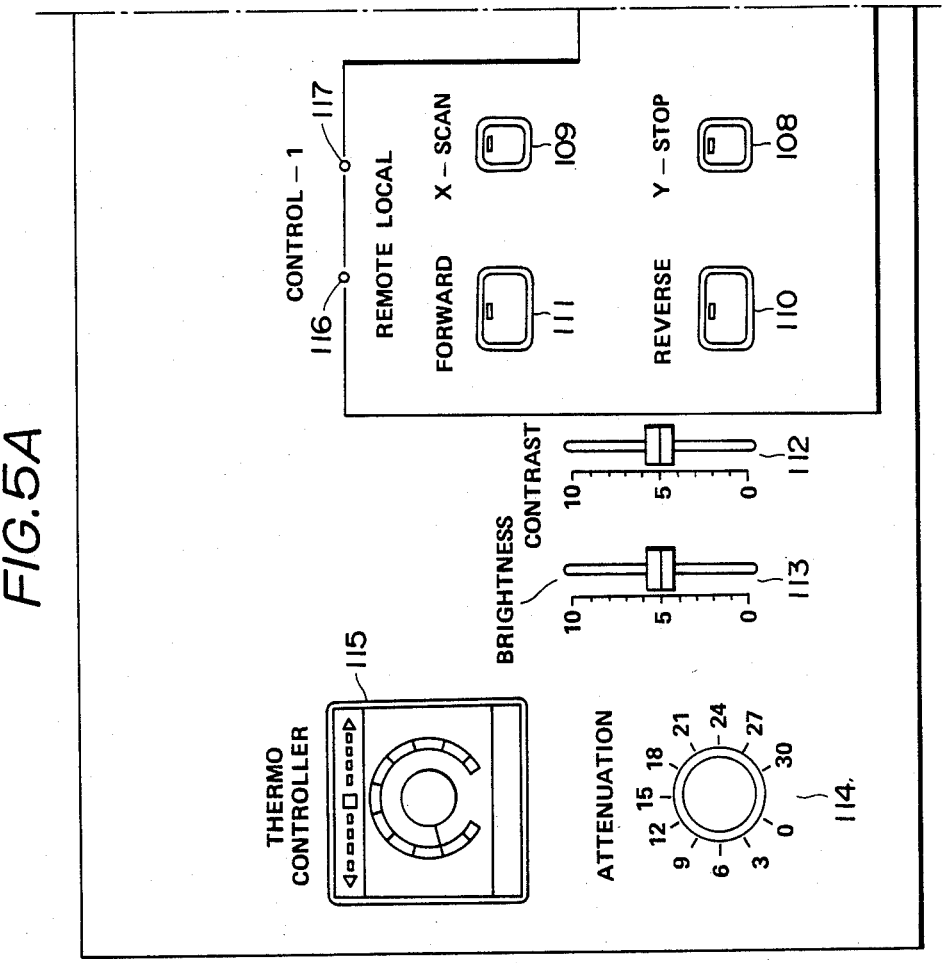

SAMPLE STAND ADJUSTING DEVICE IN AN ULTRASONIC MICROSCOPE

FIELD OF THE INVENTION AND RELATED ART STATEMENT

This invention relates to ultrasonic microscopes and more particularly to an ultrasonic microscope sample stand adjusting device wherein, in scanning and observing with a converged ultrasonic beam on a predetermined observing plane of a sample mounted on the sample table of the sample stand, the above mentioned plane of the sample can be easily made to coincide with a scanned plane so that a correct image for each minute step in the depth direction of the sample may be obtained.

The ultrasonic microscope is a device wherein a predetermined plane of a sample is two-dimensionally scanned to image sample information on the plane.

FIG. 1 is a formation view showing the principle of an ultrasonic microscope. A control control 1 is a circuit to generate signals 1a, 1b, 1c, 1d and 1e respectively controlling as predetermined a high frequency transmitting portion 2, signal receiving portion 8, X-direction scanning portion 9, Y-direction scanning portion 10 and scan converter 11. The high frequency burst signal 2a of an ultrasonic band by the above mentioned signal 1a and the output is put into a piezoelectric transducer 4 through a circulator 3. This piezoelectric transducer 4 is a reversible converter of electric signals and ultrasonic signals. The converted and obtained ultrasonic waves are converged by an acoustic lens 5 and are projected as a minute spot onto a plane of a sample 7 through such ultrasonic wave transmitting medium 6 such as, for example, water. These projected ultrasonic waves are reflected in response to the acoustic characteristics of the sample 7, are received by the acoustic lens 5 and are converted to an electric signal which is fed to the receiving portion 8 again throuth the circulator 3. This signal 3a fed to signal receiving portion 8 is gated here by a gate signal 1b from the control portion 1 to have unnecessary signals removed. It is then amplified and detected to become a detecting output signal 8a conforming to the information of the sample 7, that is, corresponding to the reflection intensity. The thus obtained detecting output signal 8a is led to the scan converter 11 together with the synchronous signal relating to the scanning of the sample 7 from the X-direction scanning portion 9 and Y-direction scanning portion 10 and is here recorded as a brightness signal. The signal 1e from the control portion 1 converts the recorded signal to a television signal, reads it out and displays it on the displaying portion 12. Also, the X-direction scanning portion 9 moves the acoustic lens 5 by the signal 1c in the X-direction with respect to the plane of the sample stand 13 (at a high speed) and the Y-direction scanning portion 10 moves the sample stand 13 in the Y-direction (at a low speed). Thereby, the sample 7 mounted on the sample stand 13 will be scanned by the ultrasonic beam from the acoustic lens 5.

In the above mentioned ultrasonic microscope, in case the internal information of the sample is to be observed, it will be necessary to move the acoustic lens 5 in the Z-direction as well. The converging spot of the ultrasonic waves converged by the acoustic lens 5 (the ultrasonic beam in the focus position) is made to coincide with an observing plane of the sample.

In the above mentioned internal observation with the ultrasonic microscope, the information of the internal plane of the sample of each minute step can be accurately obtained by making the observing plane of the sample coincide with the ultrasonic wave scanning plane formed by the converging spot. Therefore, as an initial adjustment in the observation, it is necessary to make the inclination of the observing plane of the sample mounted on the sample stand accurately coincide or be parallel with the above mentioned scanned plane. If the sample plane inclines to the scanned plane, the reflected waves will not be able to be accurately received and the picture image will become unclear. The adjustment of such inclination is indispensable particularly to knowing the integrated structure of the semiconductor. Therefore, a goniometer by which the parallel degree of planes relating to two directions can be adjusted has been conventionally used for the sample stand 13. In its adjustment, there is a difficulty in adjusting the goniometer several times so that the interference stripes appearing in the picture image when not parallel may decrease, while observing the picture image displayed in the displaying portion 12 by repeating the scanning several times in order to make the plane of the sample 7 parallel with the scanned plane formed by the converging spot of the ultrasonic beams. Therefore, most of the observing time is spent for the adjustment and thus the efficiency of using the ultrasonic microscope is decreased.

By the way, as an example of the electric method of such adjustment without using a goniometer, it is mentioned in the Patent Gazette of Japanese Patent Laid Open No. 225349/1984 that signals corresponding to the time from the reference time of respective ultrasonic wave receiving signals in a plurality of places on the sample obtained by scanning the sample on the sample stand with ultrasonic beams until the time of receiving them are respectively detected and the inclination of the above mentioned sample stand is adjusted so that both signals may be equal to each other.

OBJECT AND SUMMARY OF THE INVENTION

The present invention has it as an object to provide an ultrasonic microscope sample stand adjusting device wherein a three-dimensional inclination of a sample plane to a scanned plane formed by an ultrasonic scanning beam is automatically computed and the digital value of a required adjusting amount obtained as a result is referred to so as to be able to manually adjust the sample stand.

In order to attain the above mentioned object, according to the present invention, a distance Zo between any one point o on a sample plane and an acoustic lens made to coincide with the focal distance of the above mentioned acoustic lens is measured and memorized, the relative displacement Xa of the sample and acoustic lens from the above mentioned point o to a point a in the X-direction, the relative displacement Yb of the same from this point a to a point b in the Y-direction and the relative moving distances $|Za-Zo|$ and $|Za-Zb|$ (where Za and Zb are distances between the respective points a and b and the acoustic lens) of the above mentioned acoustic lens and the sample in the Z-direction when the acoustic lens is focused at the respective points a and ab are measured and memorized, the inclination of the sample is known on the basis of the scalar data of these respective measured and memorized distances and the sample stand is manually adjusted in conformity with the index of the required adjusting amount so as to make the above mentioned sample plane coincide or parallel with the scanned plane.

BRIEF DESCRIPTION OF THE DRAWINGS

FIGS. 5A–B are an explanatory view showing a front panel of an ultrasonic microscope body.

DETAILED DESCRIPTION OF PREFERRED EMBODIMENTS

In the below explained embodiment, the inclination of a sample, that is, the inclincation of a sample stand 32 to a scanned plane can be adjusted by the inclination of an adjusting angle automatically or by indicating a picture image by utilizing a computer system 31.

Figure 1:
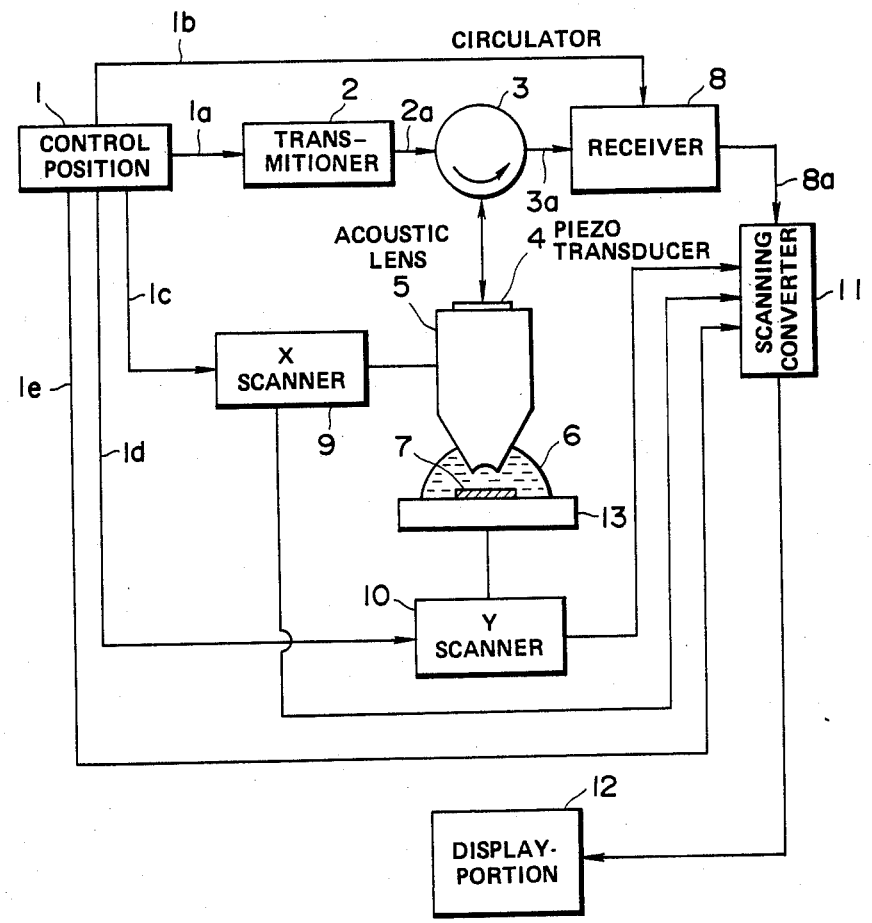
FIG. 1 is a principle formation view for explaining the principle of an ultrasonic microscope relating to the present invention.
Figure 2:
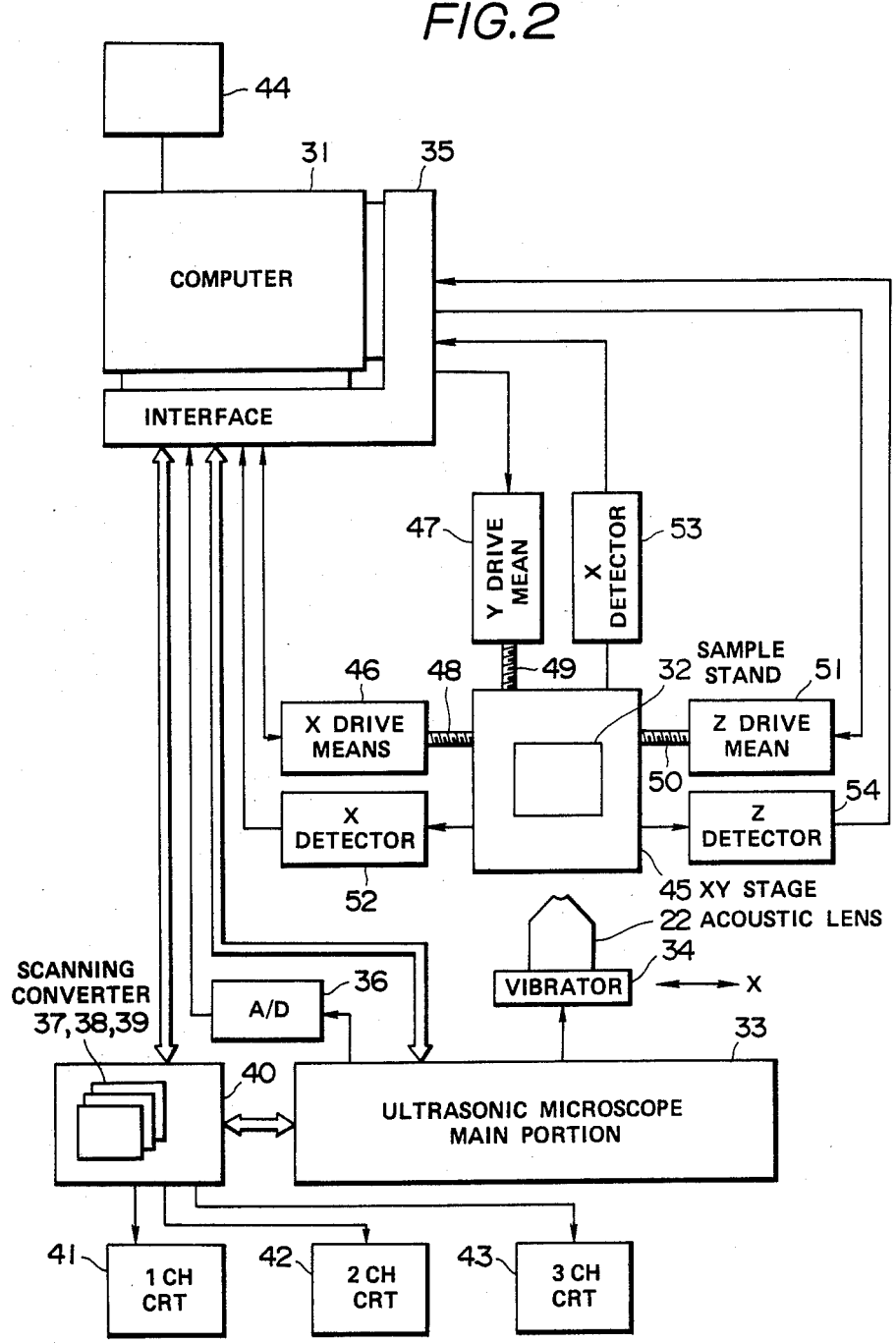
FIG. 2 is a block circuit diagram showing an embodiment of the sample stand adjusting device of an ultrasonic microscope relating to the present invention.

The reference numeral 33 represents an ultrasonic microscope body formed of a high frequency transmitting portion, circulator and receiving portion as explained in FIG. 1. A vibrator 34 scanning an acoustic lens 22 in the X-direction is fed with a scanning signal X from a computer (which shall be abbreviated as a CPU hereinafter) 31 through an interface circuit 35. The body 33 leads as a digital signal an electric signal out of the receiving portion into an interface circuit 35 through an analog-digital converter 36. This signal can be transferred to a scan converter 40 having three picture image memories 37, 38 and 39 by the CPU 31. The above mentioned three picture image memories 37, 38 and 39 are connected respectively to circuits CRT 41, CRT 42 and CRT 43.

Here, the above mentioned scan converter 40 has three memories and is provided with the circuits CRT 41, 42 and 43 for three channels, because if scanned with a minute step unit in the Z-direction, the picture image obtained in the preceding step will be held on the picture surface so that the internal information of the sample may be easy to catch (therefore the picture image before two steps may be monitored) and a PGB signal may be synthesized with picture images for three channels. The main circuit CRT 44 is a color picture image displaying device therefor.

Now, the reference numeral 45 represents an X-Y stage holding the sample stand 32. This X-Y stage 45 is connected through shafts 48 and 49 respectively to an X-direction driving means 46 and Y-direction driving means 47 formed of step motors as main bodies. The X-Y stage 45 is further connected to a Z-direction driving means 51 through a shaft 20. The respective X, Y and Z-direction driving means 46, 67 and 51 can move the stage 45 in the respective directions with driving signals from the CUP 31. Thereby, the position of the sample stand 32 can be adjusted and the sample can be made to conform to the observing range by the acoustic lens 22.

Also, the displacements in the X, Y and Z-directions of the X-Y stage 45 can be detected respectively by X, Y and Z-direction displacement detecting means 52, 53 and 54 having as main bodies encoders detecting rotary pulses from the motors forming the respective driving means. Their detected signals are fed to the CPU 31 through the interface 35. In this embodiment, the signals detected by the X-direction and Y-direction displacement detecting means 52 and 53 among detecting means 52, 53 and 54 are utilized to adjust the inclination.

An example of the mechanism of the sample stand 32 shall be explained in the following with reference to FIG. 3.

Figure 3:
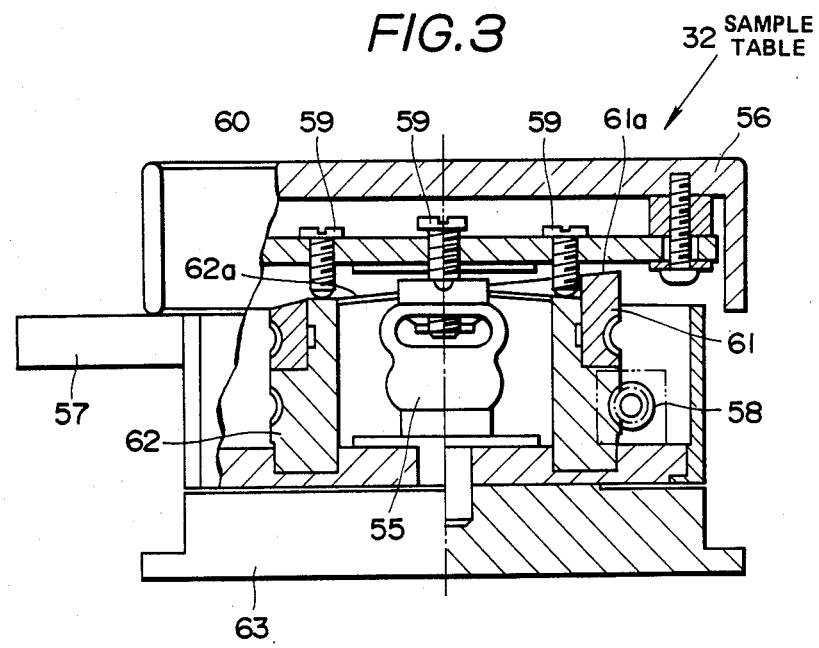
FIG. 3 is an explanatory view for explaining the mechanism of a sample stand driving means in the above mentioned device.

In FIG. 3, the sample stand 32 itself forms a goniometer so that a table 56 pulled down by an expansion joint 55 can be rotated independently by a predetermined angle with the X and Y-directions respectively as axes. More particularly, the table 56 is supported by worm bodies 61 and 62 having respectively annular slopes 61a and 62a in directions intersecting rectangularly with each other through a plate member having screws 59,59 and 59(59) arranged opposed to each other by 180 degrees. The worm bodies 62 and 61 are screwed respectively to the above mentioned worm adjusting bars 57 and 58 and are coaxially assembled and the slope 62a and the worm body 62 is positioned on the periphery of the slope 61a of the worm body 61. By this formation, the table 56 can have the inclination angle freely adjusted by the screws 59 in contact with the slopes 61a and 62a of the worm bodies 61 and 62 being moved up and down by the adjustment of the sdjusting bars 57 and 58. By the way, the reference numeral 63 represents a base.

Figure 4A:
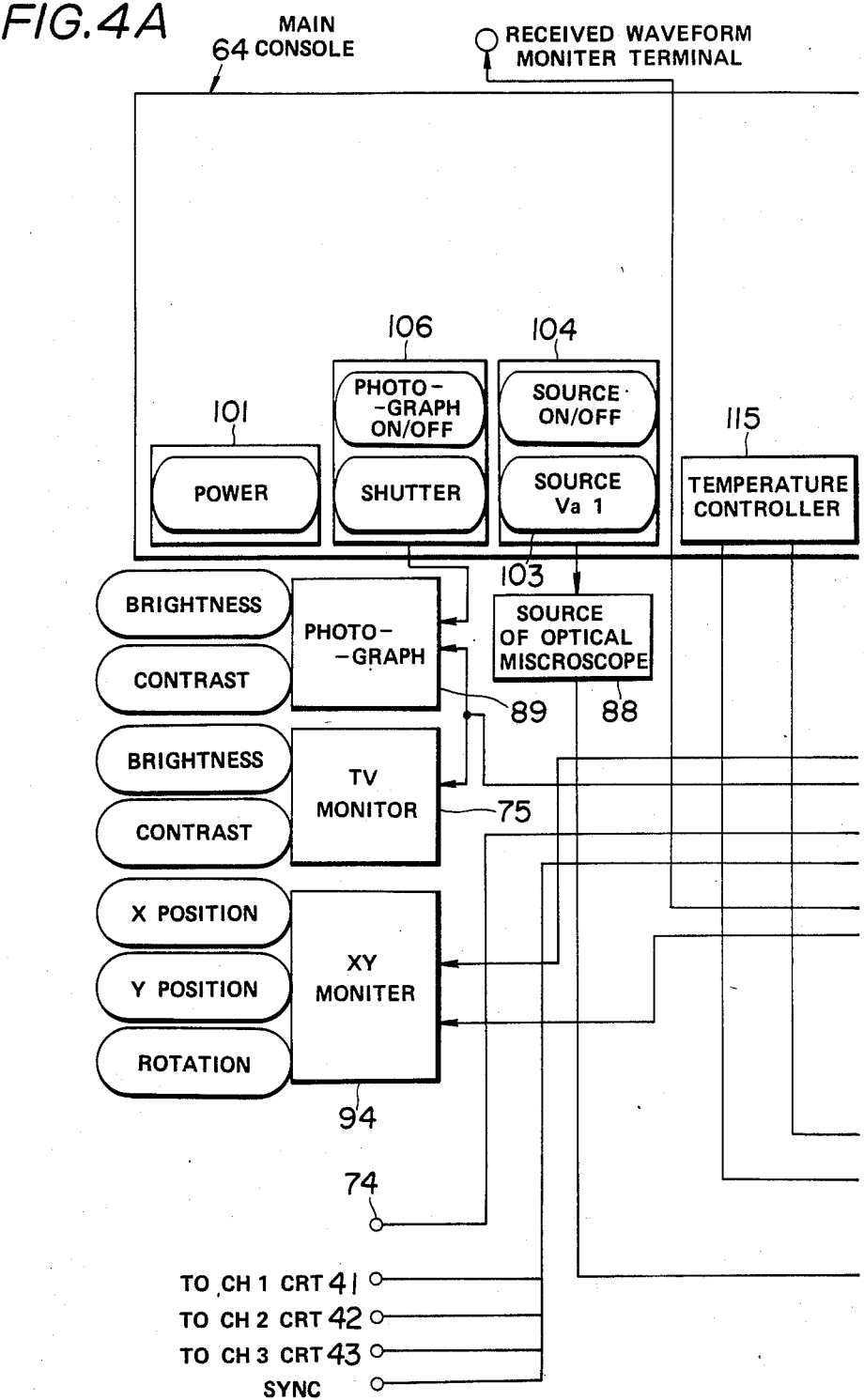
FIGS. 4A–C are general schematic view of an ultrasonic microscope adopting the above mentioned device.
Figure 4B:
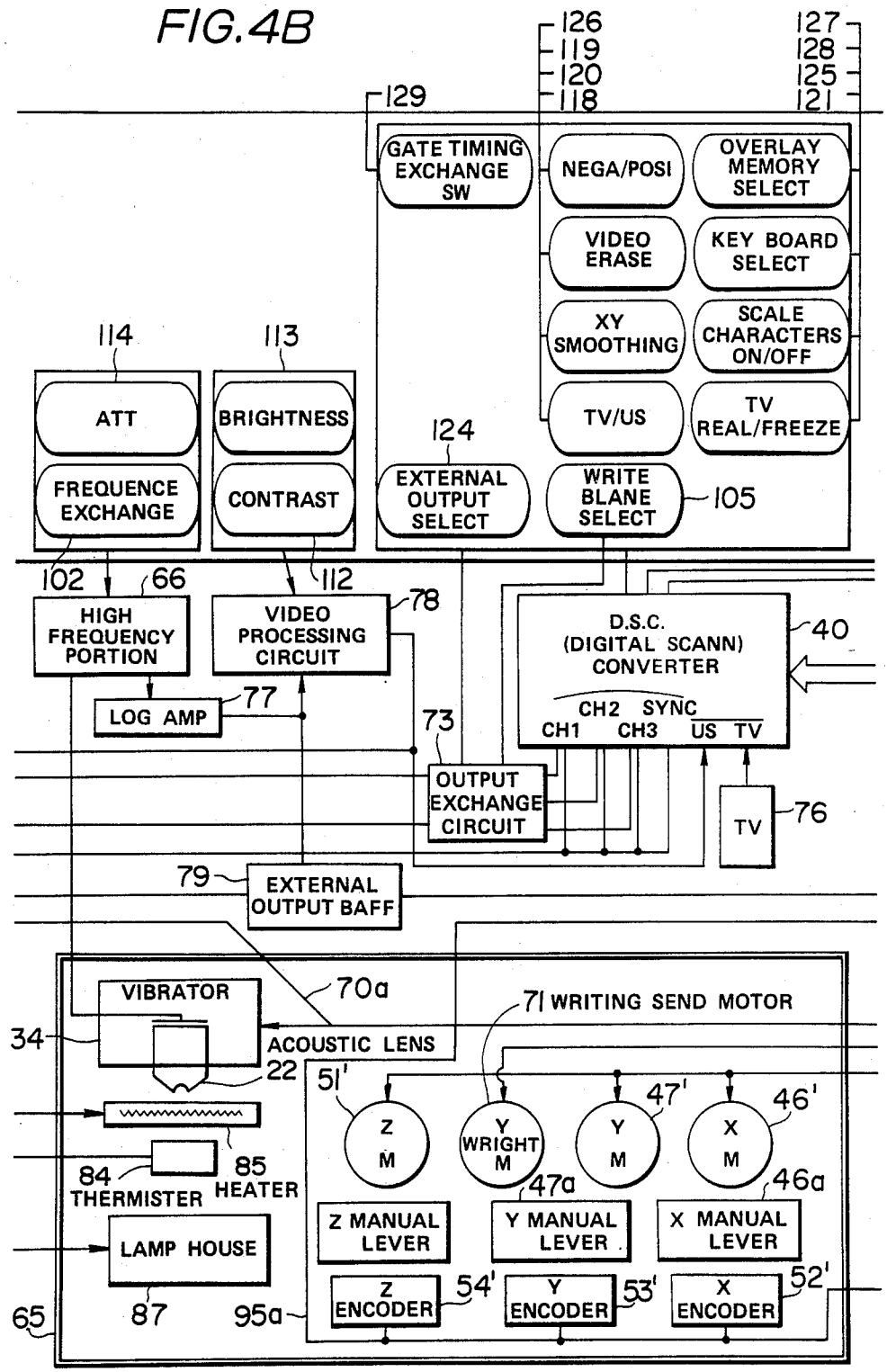
Figure 4C:
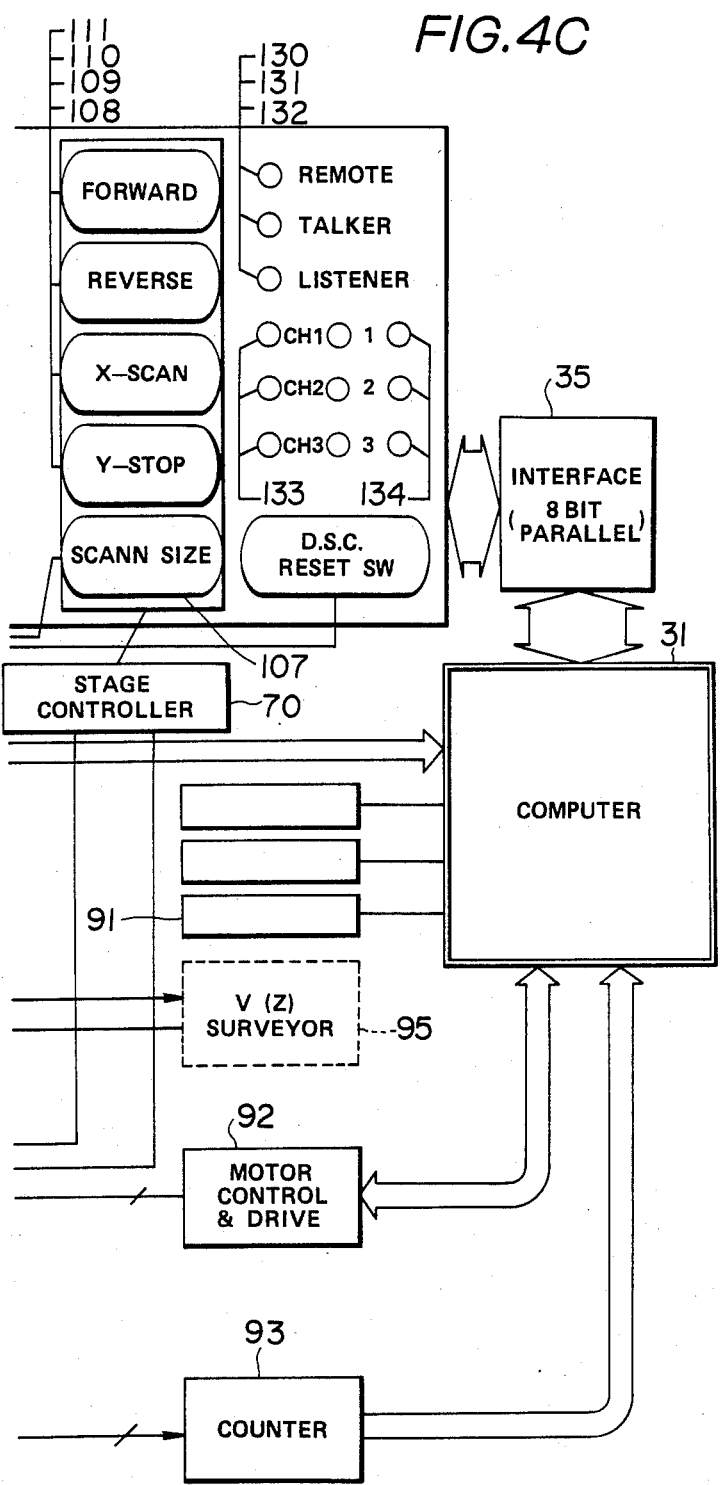
Figure 5B:
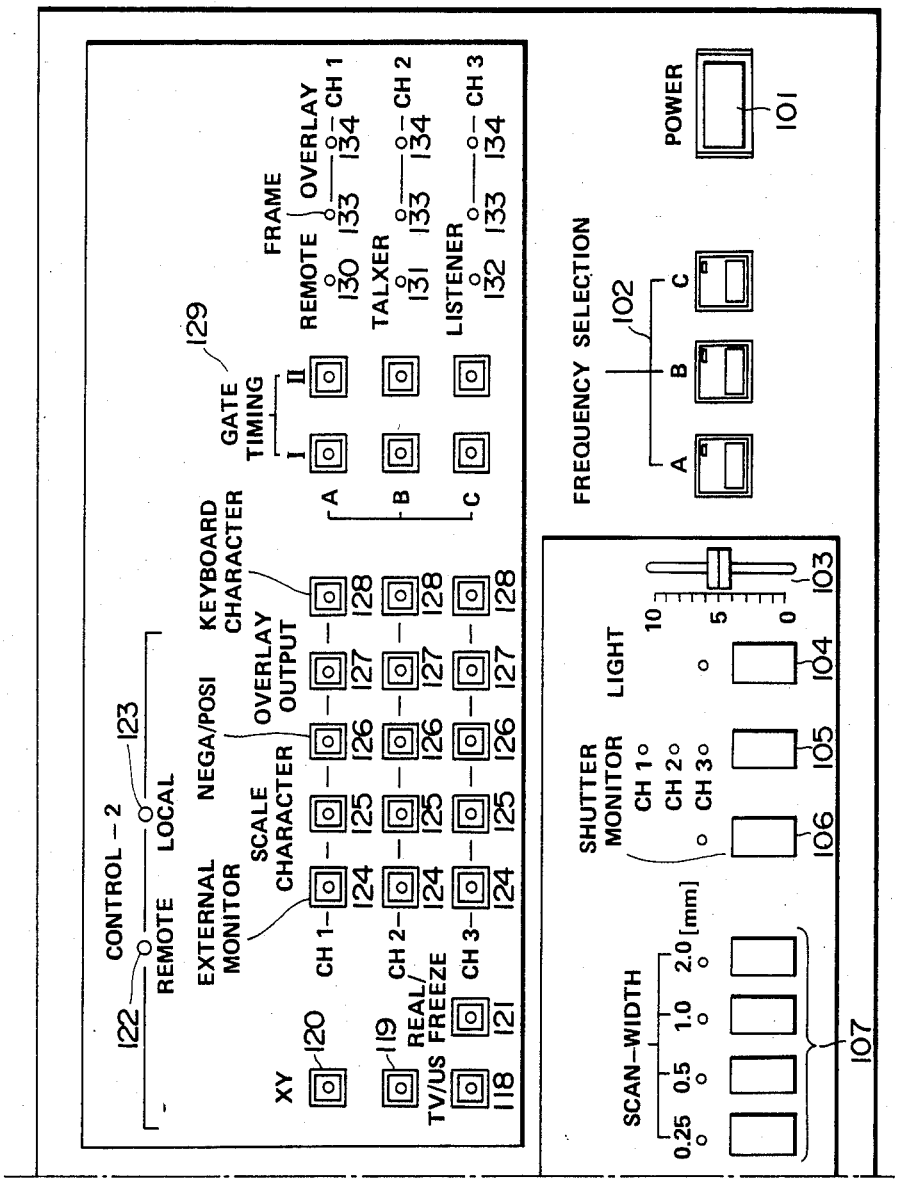
Figure 6:
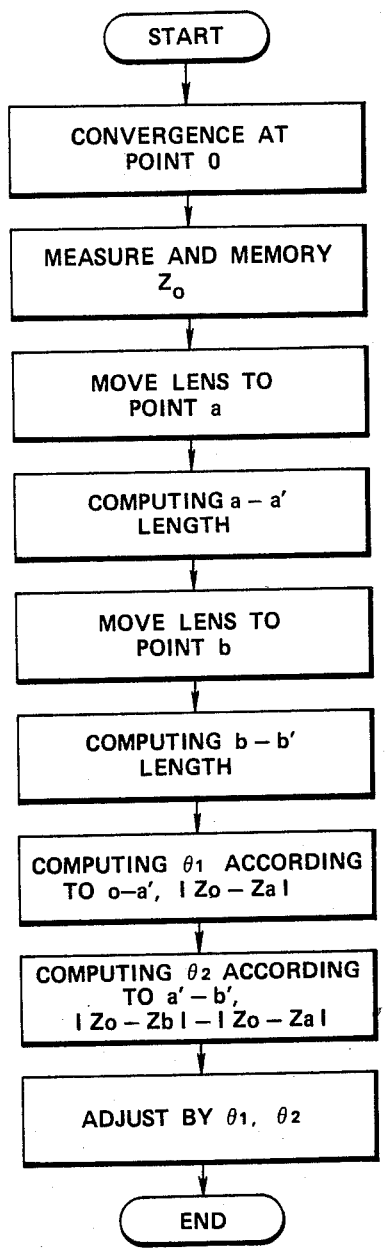
FIG. 6 is a flow chart showing an example of an adjusting operation in the present invention.

This embodiment is realized by such formation as is mentioned above but shall be explained more particularly with reference to FIGS. 4 and 5.

In FIG. 4, the same reference numerals are attached to the functional portions corresponding to those in FIG. 1, each ellipse represents a switch or adjustable grip for selecting the function mentioned therein and the circle represents a monitor lamp. The operating portion 64 in FIG. 4 corresponds to the operating panel arrangement view in FIG. 5. That is to say, the reference numeral 101 represents a power switch for switching on/off the current source;

102 represents a frequency switching switch for selecting the frequency of the signal generated in the high frequency portion 66;

103 represents a light amount volume for controlling the brightness of a lamp house 87 by operating an optical microscope light source controller 88.

104 represents a switch for switching on/off the light source;

105 represents a writing plane selecting switch for controlling the scan converter 40 and its output switch 73 whose output is input to the photographing TV monitor 75;

106 represents an on/off and shutter switch for the photographing device 89 which can bird-copy a picture image displayed in the above mentioned TV monitor 73;

107 represents a scan size switching switch for selecting an X-direction scan range and for switching as determined the scan converter 40 at the time of switching the size;

108 represents a Y-stopping switch for stopping the Y-direction scan during the scanning;

109 represents an X-scanning on/off switch for switching on/off the scanning in the Y-direction;

110 represents a reverse writing-in switch for starting the writing in of an ultrasonic image;

111 represents a forward writing-in switch for starting the writing in of an ultrasonic image and, by the way, when this is written in, the Y-stopping switch will be set in a released state;

112 represents a contrast volume for adjusting the video signal contrast at the time of the scan converter input;

113 represents a brightness volume for adjusting the video signal brightness at the time of the scan converter input and this volume and the above mentioned contrast volume 112 are connected to a video processing circuit 78 for processing an electric signal from the high frequency portion 66 through the logarithmic amplifier;

114 represents an attenuator switching volume for adjusting the intensity of ultrasonic beams by controlling the attenuation of the signal generated by the high frequency portion;

115 represents a temperature controller wherein a heater 85 is arranged below the table 32 in FIG. 3 and the thermister 84 operating point of this heater 85 is switched, which keeps a constant attenuation amount of ultrasonic wave;

116 represents a control group 1 remote state indicating LED which will light when the control group 1 is controlled with a microcomputer;

117 represents a control group 1 local state indicating LED which will light when the control group 1 can be controlled with a switch on the panel;

118 represents a TV/US switching switch for switching the input signal to the scan converter, the TV is selected in case the video signal from the TV camera 76 is to be processed with the scan converter 40 and the US is selected in case the video signal from the video processing circuit 78 is to be processed;

119 represents an erasing switch for erasing the contents of the picture image memory selected by the switch 105;

120 represents an XY correlated on/off switch for switching on/off the smoothing of ultrasonic waves;

121 represents a real/freezing switch for switching on/off the memory when a TV camera signal is put in and, when the memory is on, "FREEZE" will be made;

122 represents a control group 2 remote state indicating LED which will light when the control group 2 is controlled with a microcomputer

123 represents a control group 2 local state indicating LED which will light when the control group 2 can be controlled with a switch on the panel;

124 represents an external monitor output switching switch for selecting one memory channel for the external monitor;

125 represents a scale and character on/off switch for switching on/off the scale and character indicated on the picture surface;

126 represents a NEGA/POSI switching switch for nega/posi switching the picture image output;

127 represents an overlay output on/off switch for switching on/off an overlay memory output;

128 represents a keyboard character output on/off switch for switching on/off a keyboard character output;

129 represents a gate timing switching switch for selecting one of two set gate timings;

130 represents a remote state indicating LED which will light when the scan converter is controlled with a microcomputer;

131 represents a talker state indicating LED which will light when the contents of the picture image memory of the scan converter are transferred to the computer;

132 represents a listener state indicating LED which will light when the computer is writing in the memory of the scan converter;

133 represents a GP-IB access channel indicating LED indicating the channel of the scan converter approached by the computer.

134 represents a GP-IB access overlay memory indicating LED indicating the overlay memory of the scan converter approached by the computer.

Further, the controlling functions (108 to 111) of the group 1 are connected to the stage controller 70 so that, when the respective X-direction scans are switched on/off, the Y-direction scan is operated or stopped or the scan size is varied, the XY stage 45 and vibrator 34 will be controlled through the stage controller 70. However, the XY stage 45 is scanned with a motor 71 exclusively for the Y writing in, so that the feed in the Y-direction may be adjusted to be of a timing adapted to the writing in as synchronized with the scanning in the X-direction by a stage controller 70. Also, the stage controller 70 transmits a signal 70a for monitoring the scan size to an XY monitor 94. As the scan size is monitored by the XY monitor 94, by operating XY manual levers 46a and 47a, the position of the sample with respect to the acoustic lens 22 can be accurately met.

By the way, the reference numerals 46', 47' and 51' represents motors respectively for X, Y and Z-direction driving means 46, 47 and 51. 52', 53' and 54' represent encoders respectively for X, Y and Z-direction displacement detecting means 52, 53 and 54. The respective motors 46', 47' and 51' are driven by a controller/driver 92 controlled by the CPU 31. The outputs of the encoders 52', 53' and 54' are put into the CPU through a counter 93.

The reference numeral 94 represents a surface wave velocity curve (V(z) characteristic) measuring device. This V(z) characteristc is a characteristic (See FIG. 8) of the received signal 3a when the distance between the acoustic lens 22 and sample varies. The above mentioned V(z) characteristic measuring device 94 obtains the V(z) characteristic by putting a signal from the logarithmic amplifier 77 and of a characteristic similar to the received signal characteristic into an external output buffer 79. Further, the V(z) characteristic measuring device 94 senses that the obtained V(z) characteristic has reached a peak value and feeds the sensed output 95a as a counting operation controlling signal to the counter 93. The value of the counter 93 stopped by this controlling signal indicates the focal distance of the acousitc lens 22.

The operation based on the above mentioned formation shall be explained in the following with reference to FIGS. 1 to 9.

Figure 7:
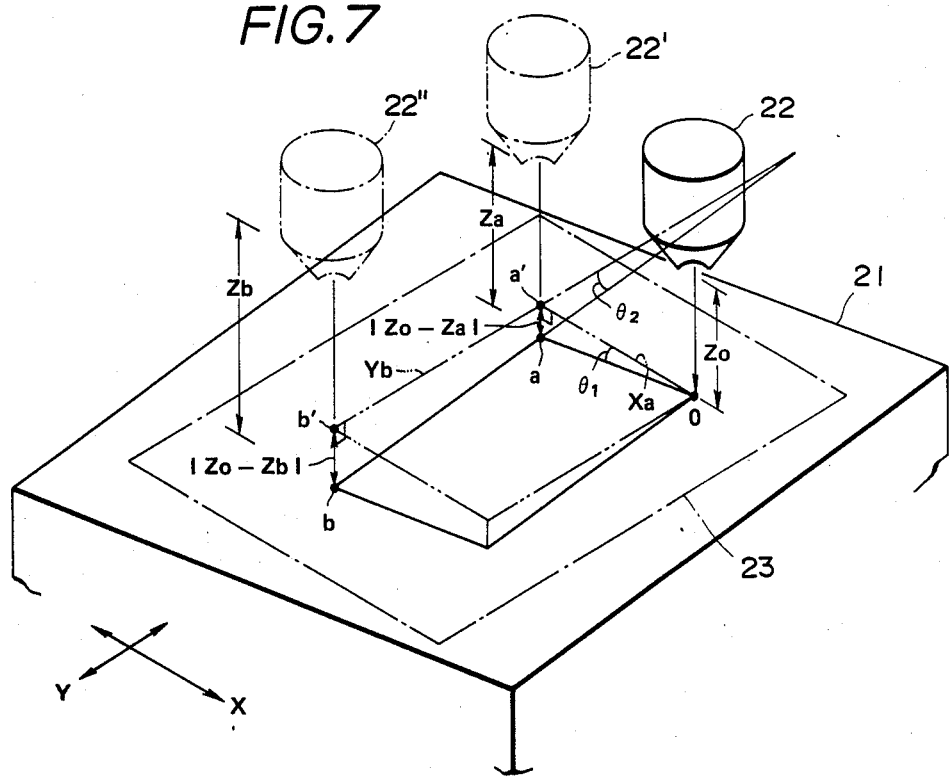
FIG. 7 is an explanatory view of the adjusting operation along the flow in FIG. 6.
Figure 8:
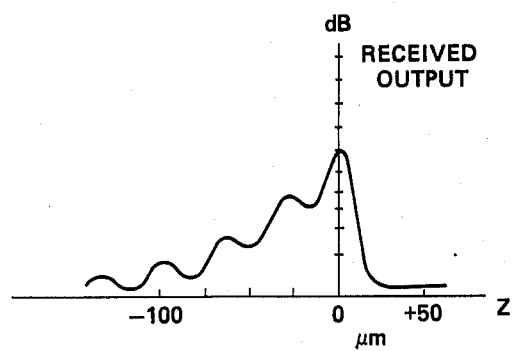
FIG. 8 is a characteristic diagram showing the received output characteristics of an ultrasonic wave beam.

In case the plane of the sample 21 mounted on the sample stand 32 is oblique to the scanned plane 23 formed by the ultrasonic beam spot of the acoustic lens 22 as shown in FIG. 7, in making the scanned plane 23 coincide with the sample plane, the CPU 31 will first focus the acoustic lens 22 at any position point o on the sample plane. WHen the acoustic lens 22 is moved far from and near to the sample 21, the received output of the acoustic lens 22 will reach a maximum value. Therefore, by detecting the value at this time it can be known, whether the acoustic lens is focused or not. By the way, it is found that this value is led by the output characteristic (so-called V(z) characteristic) of the acoustic lens, the received output value periodically rises and falls against the distance between the lens and sample shown in the abscissa as shown in FIG. 8 and, when the focal distance is 0, the maximum output will be obtained. In this device, it can be confirmed that, when the output of the external output buffer indicated by the reference numeral 79 in FIG. 4 reached the maximum peak value, the distance between the lens and sample coincide with the focal distance of the acoustic lens 22.

When the lens is thus focused, the CPU 31 will measure and memorize the distance Zo between the acoustic lens 22 and sample 21 on the print o. When this process ends, the CPU 31 will feed a signal of moving the acoutic lens 22 by predetermined steps in the X-direction to the step motor 46' of the X-direction driving means 46 through the controller/driver 92. If the point to which the acoustic lens 22 is moved by the predetermined steps in the X-direction is a point a, the CPU 31 will measure the distance Zo−Za, between the point a and a point a' corresponding to the point a on the scanned plane. In this case, the acoustic lens 22 will put out the maximum peak value conforming to the V(z) characteristic in its position 22' by being moved in the Z-direction and therefore the displacement then, that is, the movement from the initial position (point o) when moved by the predetermined steps parallel along scanned plane 23 will be determined by counting with the counter 93 the pulses from the encoder 54' and thereby the CPU 31 will be able to determine Zo−Za (the distance between a−a'). Further, also when the acoustic lens 22 is moved (parallel in the Y-direction) to the position 22', $|Zo-Zb|$ (the distance between b−b') will be able to be determined by the same means. By the way, for the displacements respectively in the X and Y-directions, the pulses generated respectively by the X-direction step motor 46' and Y-direction step motor 47' are pulsed respectively by the encoders 52' and 53' and are counted by the counter 93 and the CPU 31 uses the pulse counts for the operation.

Figure 9:
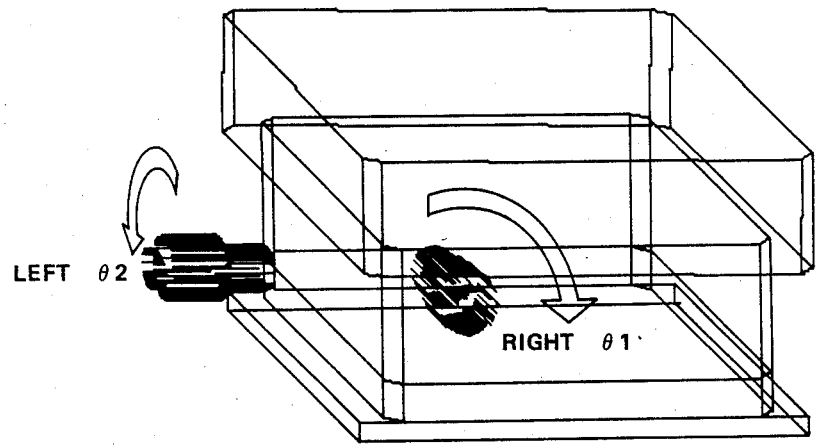
FIG. 9 is a computer graphic view showing an example of a picture surface indicating a required adjusting amount by a computer.

As in the above, the Zo and distances o−a', a−a', a'−b' and b'−b can be known by the CPU 31., Here, the angle $\theta_1$ made by the distances o−a' and o−a can be easily operated by $|o-a'|$ and $|Zo-Za|$ and the angle $\theta_2$ made by b−a and b'−a' can be operated by $|b'-a'|$ and $(|Zo-Zb|-|Zo-Za|)$. Therefore, the CPU 31 can determine $\theta_1$ and $\theta_2$. In the present device, the above mentioned $\theta_1$ and $\theta_2$ are indicated in the CRT (not illustrated) of the shape of the sample stand 32 as shown in FIG. 9 so that the adjuster may known $\theta_1$ and $\theta_2$, that is, the three-dimensional inclinations of the sample plane to the scanned plane 23 and may accordingly properly adjust the table 56. By the way, according to the present invention, the amount of one step in the Z-direction is, for example, 1 μm., the Z-direction moving distance indicating resolving power is 0.5 μm. And the inclination can be corrected in a range of the maximum of −5 degrees.

By the way, the above mentioned embodiment is an example but the present invention can be variously modified without deviating from the appended claim.

As explained above, according to the present invention, there is an effect that a sample plane to be observed can be quickly and precisely made parallel with a plane two-dimensionally scanned with an ultrasonic beam converging spot and there is an advantage that, as it is made by the instruction of a computer, such technique as the skill of the adjuster is not required.

What is claimed is:

1. An ultrasonic microscope sample stand adjusting device comprising:

an ultrasonic beam transmitting and receiving means having an acoustic lens, for transmitting an ultrasonic wave as a beam through said acoustic lens and for outputting the ultrasonic wave received by said acoustic lens as an electric signal for displaying a picture image by scanning on a sample surface;

a sample table means disposed opposite said ultrasonic beam generating means to support a sample mounted thereon;

a sample stand driving means for moving either one of said sample table means and said acoustic lens relative to one another in X, Y and Z-directions;

a three-dimensional measuring and memory means, at three positions to determine the sample surface plane for scanning, as distance Zo in the Z direction which distance coincides with the focal distance of said acoustic lens at a first position 0, displacement Za−Zo in the Z direction which is defocus value at a second position A, displaced Xa from the first position 0, in the X direction and displacement Zb−Zo in the Z direction which is another defocus value at a third position B, displaced Yb from the first position 0 in the Y direction;

a computing means for computing the inclination of said sample plane with respect to the X-Y plane for scanning on the basis of the scalars Zo, Za−Zo, Zb−Zo, Xa and Yb of said distances memorized by said distance measuring and memory means; and a table inclination means for making said sample surface plane coincide or become parallel with the scanned plane in conformity with the operation data from the computing means.

2. The ultrasonic microscope sample stand adjusting device of claim 1, wherein said table inclination means is comprised with two independent angular adjustments.

3. The ultrasonic microscope sample stand adjusting device of claim 2 wherein said independent angular adjustments are comprised of worm bodies having respective angular slopes, a plate parallel to said table having 2 pair of screws arranged opposed to each other by 90 degrees, wherein free tips slide on said slopes and two independent adjustment bars for each inclination, and the table is inclined in two directions rectangularly while said worm bodies are driven by said adjustment bars respectively.

* * * * *